US00PP30445P3

(12) United States Plant Patent
Wheeler et al.

(10) Patent No.: US PP30,445 P3
(45) Date of Patent: Apr. 30, 2019

(54) BLUEBERRY PLANT NAMED 'BB06-50FL-1'

(50) Latin Name: *Vaccinium corymbosum*
Varietal Denomination: BB06-50FL-1

(71) Applicant: Berry Blue LLC, Grand Junction, MI (US)

(72) Inventors: Edmund J. Wheeler, Holland, MI (US); James F. Hancock, Scarborough, ME (US)

(73) Assignee: Berry Blue, LLC, Grand Junction, MI (US)

( * ) Notice: Subject to any disclaimer, the term of this patent is extended or adjusted under 35 U.S.C. 154(b) by 0 days.

(21) Appl. No.: 15/530,909

(22) Filed: Mar. 20, 2017

(65) Prior Publication Data

US 2018/0271003 P1 Sep. 20, 2018

(51) Int. Cl.
*A01H 5/08* (2018.01)

(52) U.S. Cl.
USPC ..... Plt./157
CPC ..... *A01H 5/08* (2013.01)

(58) Field of Classification Search
USPC ..... Plt./157
CPC ..... A01H 5/08
See application file for complete search history.

*Primary Examiner* — Kent L Bell
(74) *Attorney, Agent, or Firm* — King IP Law; Joshua King

(57) ABSTRACT

A new and distinct cultivar of blueberry plant named 'BB06-50FL-1' as described and shown herein. 'BB06-50FL-1' is a new and distinct low chill tetraploid Southern highbush blueberry (*Vaccinium*) variety of complex ancestry, based largely on *V. corymbosum* with over 13% *V. darrowii* and small contributions of *V. angustifolium, V. tenellum*, and *V. ashei*. 'BB06-50FL-1' is a productive mid-season variety that ripens at a similar time as 'Star', U.S. Plant Pat. No. 10,675. 'BB06-50FL-1' is intended for areas that successfully grow lower chill Southern highbush varieties. The fruit of 'BB06-50FL-1' are large, typically 18 mm or more in diameter with an average berry weight of 2.9 gram per berry, well exposed on a medium upright bush with a small crown. The fruit of 'BB06-50FL-1' has very good flavor with a balanced amount of sugar and acidity and is also firm and juicy.

5 Drawing Sheets

Latin name of the genus and species of the plant claimed: *Vaccinium corymbosum.*

Variety denomination: BLUEBERRY PLANT NAMED 'BB06-50FL-1'.

BACKGROUND AND SUMMARY

Blueberries are a well-known fruit enjoyed by many throughout the world. One example of an existing, patented blueberry variety is 'Star', U.S. Plant Pat. No. 10,675. Another example of an existing, patented blueberry variety is 'Emerald', U.S. Plant Pat. No. 12,165.

Comparing 'BB06-50FL-1' to 'Star', the immature summer cane color of 'BB06-50FL-1' is olive green compared to yellow for 'Star'; the fruit of 'BB06-50FL-1' is appreciably larger in size and more rounded than 'Star'; and, the mature leaves of 'BB06-50FL-1' are shorter and less wide than the mature leaves of 'Star'.

Comparing 'BB06-50FL-1' to 'Emerald', 'BB06-50FL-1' ripens 7 days later and has a more concentrated ripening season than 'Emerald'; the bush shape of 'BB06-50FL-1' is more upright than Emerald; 'BB06-50FL-1' has much fewer upright canes than 'Emerald'; and, the mature leaf shape and size of 'BB06-50FL-1' is narrower and smaller in size than 'Emerald'.

The present cultivar, 'BB06-50FL-1', provides one or more advantages compared to these and/or other blueberry varieties.

BRIEF DESCRIPTION OF THE PHOTOGRAPHS

Figure 1:
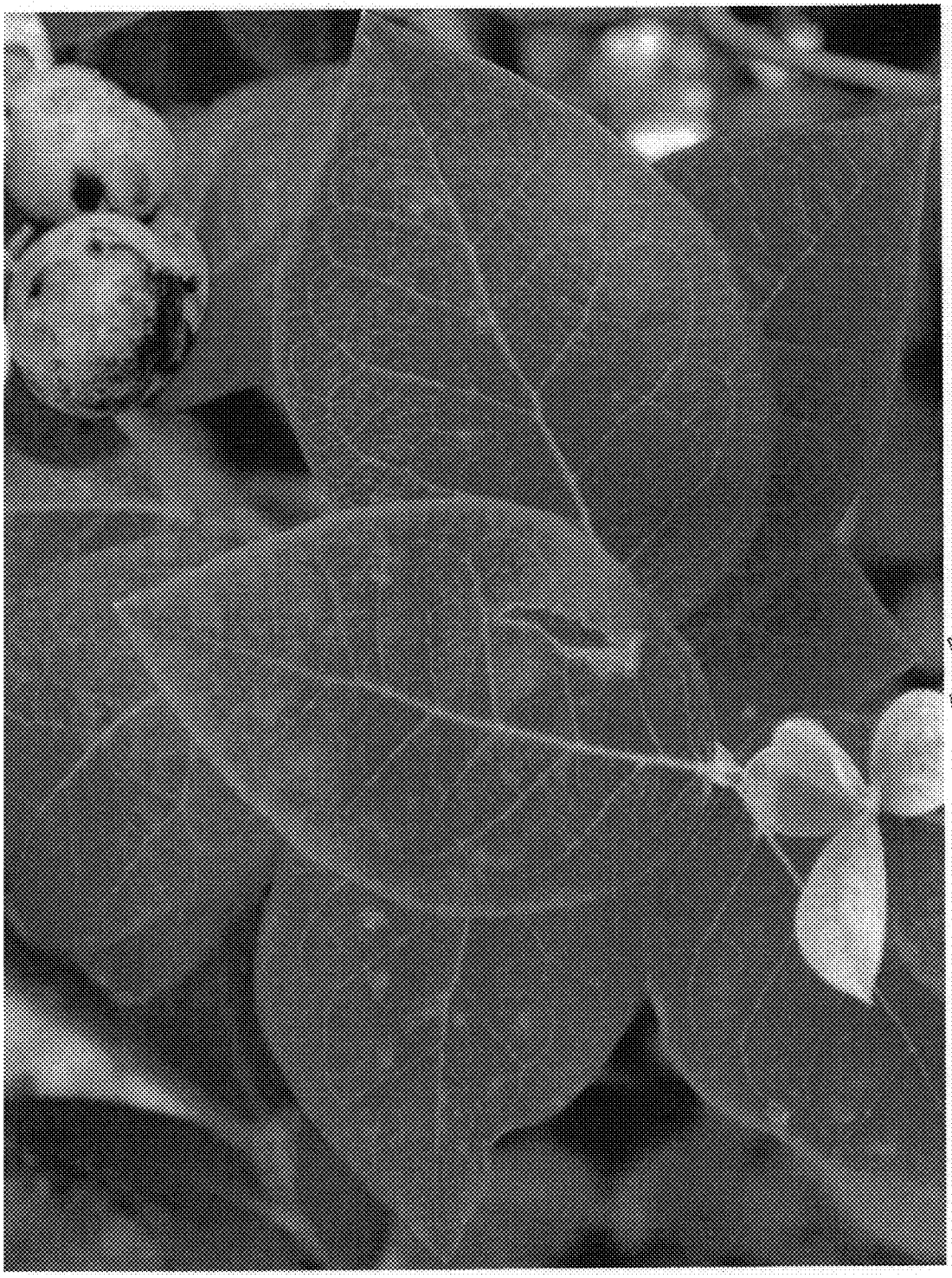
FIG. 1 is a close-up photograph of the mature leaves of 'BB06-50FL-1' showing the leaf color, shape, venation and petioles.
Figure 2:
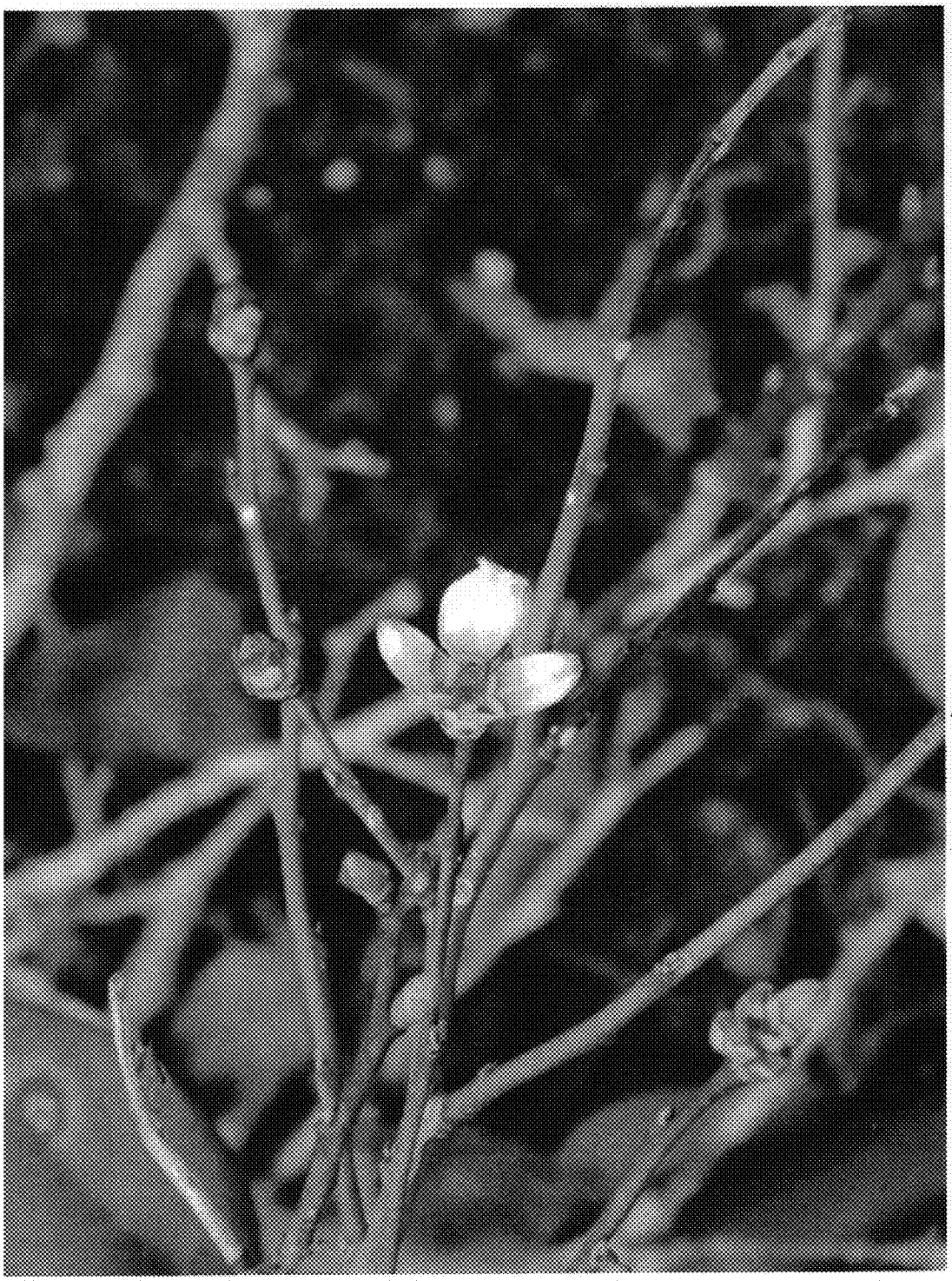
FIG. 2 is a second close-up photograph showing the winter cane color, the color and shape open and un-opened flowers and the shape and color or floral buds.
Figure 3:
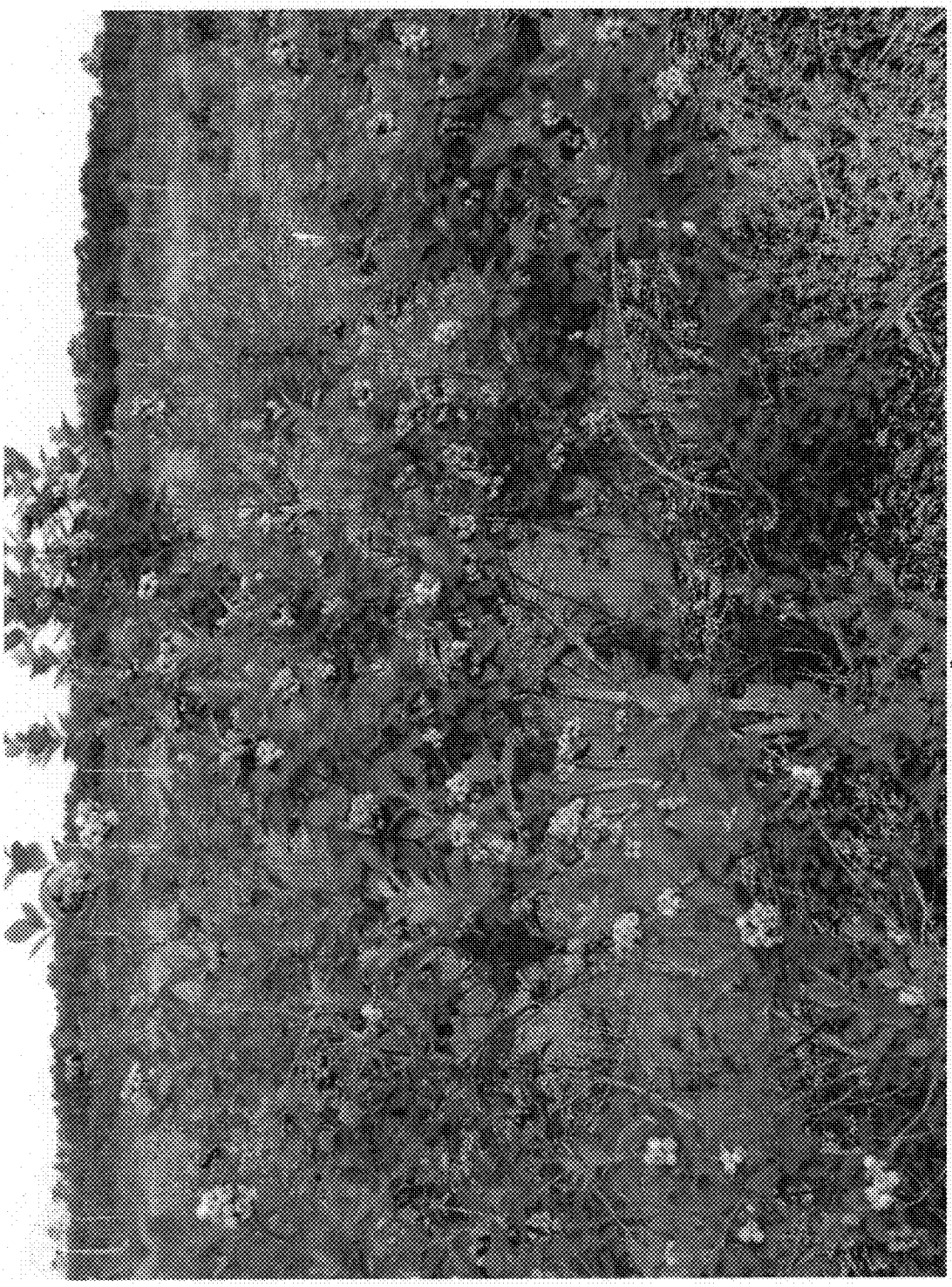

FIG. 3 a photograph showing a mature bush of 'BB06-50FL-1' in Interlachen, Fla., showing the overall bush shape, leaf color, color and structure of mature canes, the presentation of the fruit and cluster density, size and color of ripe and unripe fruit and overall yield.

Figure 4:
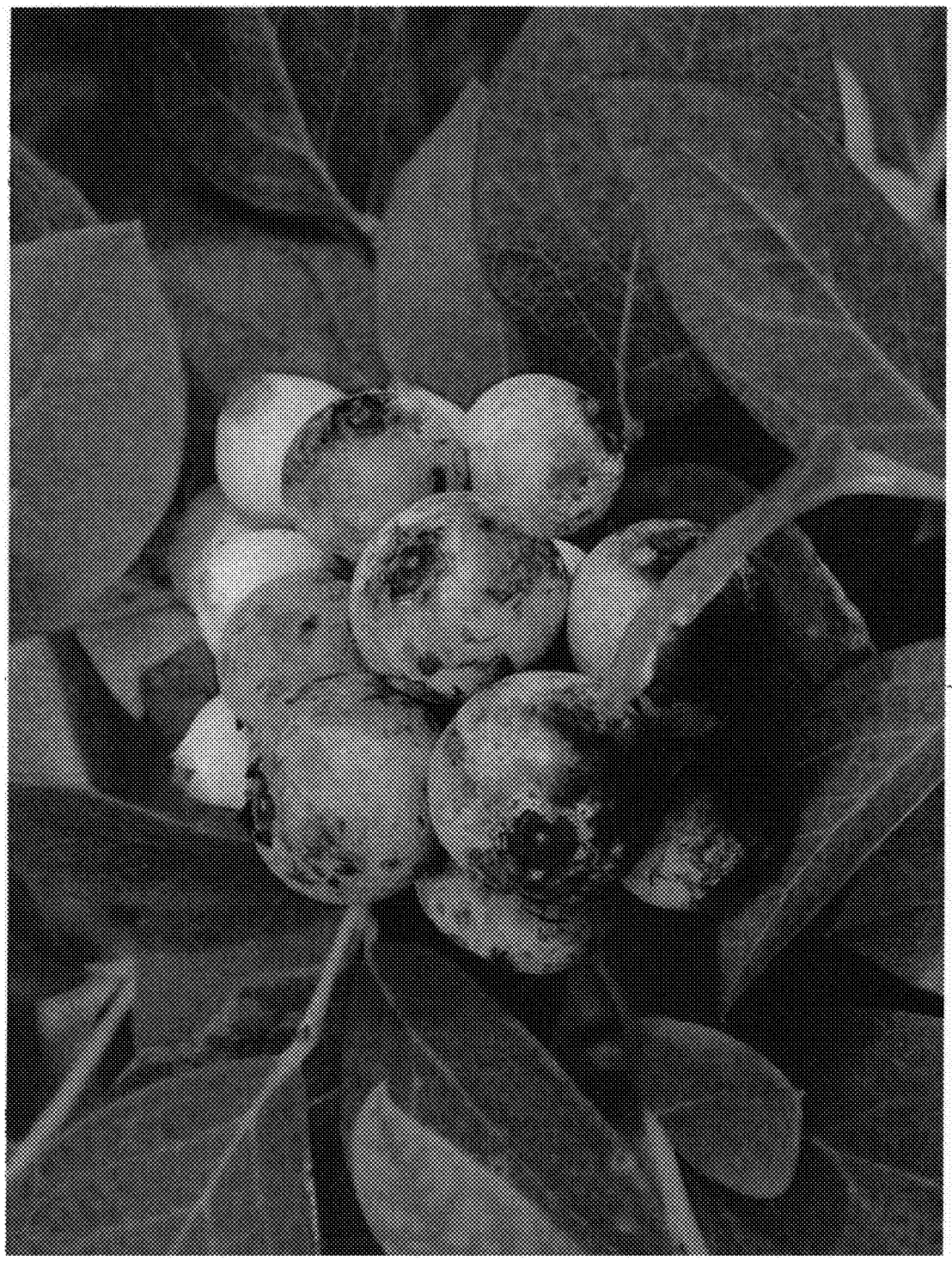

FIG. 4 is a third close up photograph of a fruit cluster of 'BB06-50FL-1' depicting the size, shape and color of ripe and unripe fruit as well as the cluster density, also the size and color of mature leaves, summer canes and leaf petioles.

Figure 5:
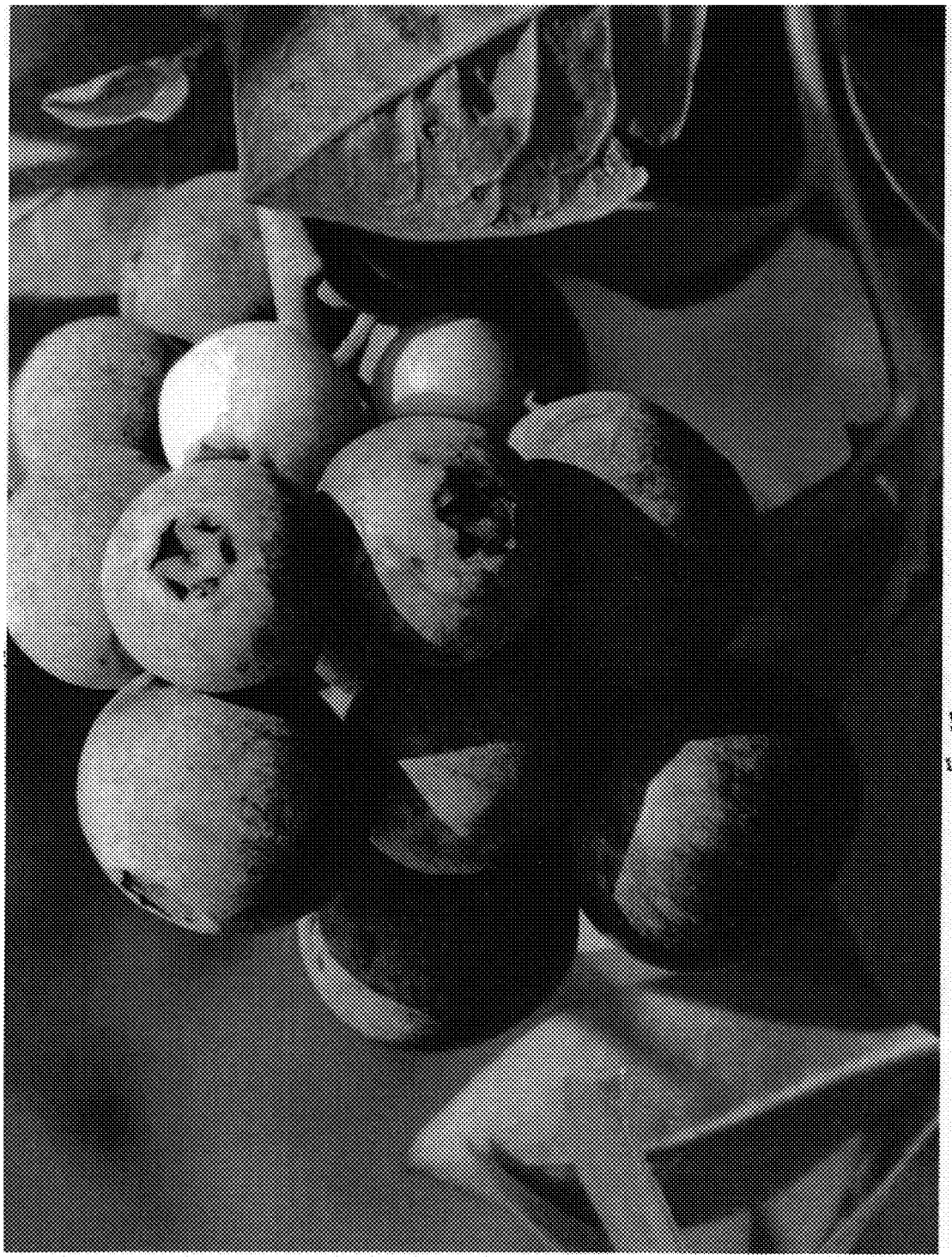

FIG. 5 is a fourth close-up photograph of a fruit cluster of 'BB06-50FL-1' depicting size, shape and color of ripe and unripe fruit and the fruit cluster density.

DETAILED DESCRIPTION

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely based on an individual bush observed in successive years through 2012, followed by three bush advanced trials in fields near Interlachen, Fla., Manor, Ga., and Homerville, Ga., in 2013, then field observations in 2015 on 5-year old plants located in advanced trial plots near Interlachen, Fla., and Manor, Ga. Laboratory analysis of fruit characteristics were done in Grand Junction, Mich. All of the bushes have retained the characteristics of the original selection.

Cultivar name: 'BB06-50FL-1'.

Classification:

*Family*.—Ericaceae.

*Botanical name*.—*Vaccinium corymbosum*.

*Common name*.—Blueberry.

Parentage:

Female parent:

Name: 'Jewel' (parents unknown).

U.S. Plant Pat. No. 11,807. Compared to 'Jewel', 'BB06-50FL-1' averages 7 to 10 days later for the date of 50% ripening, 'BB06-50FL-1' has a much larger, heavier and firmer berry than 'Jewel', and the flavor of 'BB06-50FL-1' is much sweeter and less acidic.

Male parent:

Name: 'Sweetcrisp' (parents: Southern Belle U.S. Plant Pat. No. 13,931 x FL95-3 unpatented).

U.S. Plant Pat. No. 20,027. Compared to 'Sweetcrisp' 'BB06-50FL-1' is two weeks later for the date of 50% ripening, has a heavier berry, has less sugar content and is less firm than 'Sweetcrisp'. 'BB06-50FL-1' originated as a seedling selected from a cross of 'Jewel' x 'Sweetcrisp'. The seed was germinated and plants of that cross were grown in Grand Junction, Mich., for 1 year and then planted in a seedling evaluation plot near Interlachen, Fla. The plant was first selected in the spring of 2009 based on excellent morphological and fruit characteristics and was given the number 'BB06-50FL-1' and was tested under this number in succeeding years. The individual bush was observed in successive years through 2012. Three bush advanced trials were planted in commercial fields near Interlachen, Fla., Manor, Ga., and Homerville, Ga., in 2013. These trials were evaluated in successive years. All of the observed bushes have retained the characteristics of the original selection. Softwood cuttings of 'BB06-50FL-1' were first taken in 2010 and rooted in Grand Junction, Mich., and Interlachen, Fla. 'BB06-50FL-1' has been propagated several times in succeeding years, and tissue culture microshoots have been grown in 2013 and 2015. All propagated plants have retained the original characteristics. Softwood cuttings root readily as do tissue cultured microshoots.

General description of 'BB06-50FL-1': 'BB06-50FL-1' is a new and distinct low chill tetraploid Southern highbush variety (*Vaccinium*) variety of complex ancestry, based largely on *V. corymbosum, V. ashei* and *V. darrowii*, with a limited contribution from *V. tenellum* and *V. fuscatum*. It is a very productive mid-season variety with high quality fresh market characteristics and also has excellent bush growth, vigor and bush longevity. It is intended for areas which successfully grow lower chill Southern highbush varieties. Winter chilling requirements for successful flowering and leafing are approximately 350 hours (<7° C.). Plants of 'BB06-50FL-1' are medium upright in bush habit with a modest number of primary canes and laterals. Flowering and leafing are synchronous. Flowering is early in northern Florida and southern Georgia and may require frost protection for successful pollination and maximum yields. Plant vigor is excellent and the plants appear to not be overly susceptible for foliar and soil diseases if normal horticulture practices are followed. The berries are well exposed, large to very large with a small and dry picking scar, with excellent medium blue color with a medium amount of bloom, which is modestly maintained during handling. The flavor is very good with a balance of medium amounts of sweetness and acidity. The berries are very firm with a crunchy and juicy texture with medium storage ability of 3 to 4 weeks.

References to color refer to The Pantone Book of Color, Eisemann and Herbert, Harry N. Abrams, Inc. Publishers, New York, ISBN 0-8109-3711-5, 1990. Color measurements were taken with a SpectraMagic NX Model CR410, Konica Minolta, Japan.

Morphological characteristics reference: Plant Systematics, Jones and Luchsinger, 2 Ed., McGraw Hill, New York, ISBN 0-07-032796-3, 1986.

Firmness readings: BioWorks FirmTec2, Wamena, Kans.

Average size information:

*General description*.—Medium large bush size, medium upright bush habit. 5-year plant 152 cm height, 188 cm width, height/width ratio 0.81:1.

*Growth*.—Excellent.

*Productivity*.—Very good.

*Cold hardiness*.—Leaf and flower buds −5° C., open flowers and fruit −2° C.

Specific features of the variety:

Plant:

*Growth habit*.—Medium upright.

*Plant width*.—188 cm at mid-bush.

*Plant height*.—152 cm.

*Productivity*.—7-8 lbs. per mature bush.

*Cold hardiness/tolerance*.—Leaf and flower buds −5° C., open flowers and fruit −2° C.

*Chilling requirement*.—350 hours below 7° C.

*Canes*.—Moderately branched, average 8 canes per bush, average 70-87 cm length, medium number of laterals.

*Mature cane color*.—Pantone Sand, 15-1225.

*Texture*.—Rough.

*Fruiting wood*.—Immature winter color — Pantone Burnt Henna, 19-1540, immature summer color — Pantone Green Olive, 17-0535.

*Internode length range*.—10-12 mm.

*Surface texture of new wood*.—Smooth.

*Mature canes*.—Circular in shape, 15 mm width. Average date of 50% flowering is February 5 (Interlachen, Fla.). Average date of leaf but burst is January 25 in Interlachen, Fla.

*Time of fruit ripening*.—April 28 (Interlachen, Fla.).

*Disease resistance/susceptibility*.—None claimed.

Foliage:

*Leaf color*.—Upper — Pantone, Chive. 19-0323, lower surface — Pantone Mistletoe, 16-0220.

*Leaf arrangement*.—Simple Alternate.

*Leaf margins*.—Entire.

*Leaf venation*.—Pinnate.

*Leaf apices*.—Acuminate.

*Leaf bases*.—Acute.

*Vein and petiole coloration*.—Pantone Apple Green, 15-0543.

*Petiole length*.—5 mm.

*Fall leaf color*.—Pantone Crimson 19-1762.

Leaf dimensions:

*Overall shape*.—Obtuse.

*Length*.—49-59 mm, Average 55 mm.

*Width*.—30-37 mm, average 36 mm.

*Leaf margins*.—Entire, no visible pubescence and a few nectaries.

*Leaf surface*.—Smooth upper and lower, no visible pubescence.

Leaf buds:

*Shape*.—Medium obtuse.

*Length*.—3 mm.

*Width*.—2 mm.

*Color*.—Pantone Crimson 19-1762.

Flower:

*Flower shape*.—Elongate urceolate, mostly smooth texture with a slight ridging of the corolla.

*Flower bud number*.—Medium high.

*Flowers per cluster*.—8-9.

*Flower fragrance*.—Light floral.

*Corolla color*.—Pantone Ice 11-4803.

*Corolla length*.—10 mm.

*Corolla width*.—5 mm.

*Corolla aperture width*.—4 mm.

*Flower peduncle length*.—5 mm.

*Flower peduncle diameter*.—1 mm.

*Flower peduncle texture*.—Smooth.

*Flower peduncle color*.—Pantone Peridot, 17-0336.

*Flower pedicel length*.—6 mm.

*Flower peduncle diameter*.—1.5 mm.

*Flower peduncle texture*.—Smooth.

*Flower pedicel color*.—Pantone Peridot, 17-0336.

*Calyx diameter* (*with sepals*).—3 mm.

*Calyx color*.—Pantone Peridot, 17-0336.

Stamen:

*Length*.—8 mm.

*Number per flower*.—10.

*Filament color*.—Pantone Caramel, 16-1439.

*Style*.—8 mm, top of ovary to stigma tip.

*Color*.—Pantone Cedar, 16-1439.

Pistil: Even with top of corolla.

*Ovary color*.—Pantone Cedar, 16-1439.

*Anther*.—Length: 3 mm.

*Number*.—10.

*Color*.—Pantone Caramel, 16-1439.

Pollen:

*Abundance*.—Medium high.

*Color*.—Pantone Winter White 11-0507.

Fruit:

*Date of* 50% *maturity*.—April 28 (Interlachen, Fla.).

*Duration of ripening*.—Average 22 days in Interlachen, Fla.

*Yield*.—7-8 lbs./bush.

*Immature fruit color*.—Pantone Misty Jade, 13-6008.

*Berry color with wax*.—Pantone Nightshadow Blue, 19-3919, SpectraMagic (L,a,b)-(39.23, 0.98, −2.14).

*Berry color with wax removed*.—Pantone Majolica Blue, 19-4125.

*Berry flesh color*.—Pantone Frozen Dew 13-0513.

*Berry surface wax abundance*.—Heavy persistent.

*Berry weight*.—2.9 grams/berry.

*Berry size*.—Height 15 mm, width 18 mm, aspect (H/W) 0.8.

*Berry shape*.—Oblate.

*Cluster density*.—Medium loose.

*Average number of berries per cluster*.—8.

*Average weight of fruit per cluster*.—23 grams.

*Detachment force*.—Easy.

*Self-fruitfulness*.—Fair, will need cross pollination for maximum yield and size.

*Fruit stem scar*.—1 mm diameter, 1 mm depth.

*Calyx*.—5 point.

*Calyx diameter*.—5 mm.

*Calyx depth*.—1 mm.

*Berry firmness*.—Firm, 213 grams/mm.

*Berry sweetness*.—Medium high, Brix° 11.5.

*Berry acidity*.—TA 0.40, pH 3.25.

*Berry flavor and texture*.—Balanced sugar and acidity, juicy and crunchy texture.

*Storage quality*.—Medium high, 3-4 weeks in refrigerated storage. Suitability for mechanical harvesting: very good, bush shape and crown width, berry firmness, concentrated ripening and easy detachment are very good for mechanical harvesting good potential due to firm fruit, bush shape and crown size, concentration of ripening.

Seed:

*Seed abundance in fruit*.—Medium, 10-15 seed per fruit.

*Seed color*.—Pantone Copper Brown 18-1336.

*Seed dry weight*.—NA.

*Seed size*.—1.5 mm length×0.5 mm width.

Possible typical market uses: Fresh market, processing into jams, purees and yogurt.

What is claimed is:

1. A new and distinct cultivar of Blueberry plant named 'BB06-50FL-1' as described and shown herein.

* * * * *